(12) United States Patent
Klein

(10) Patent No.: US 7,787,593 B2
(45) Date of Patent: Aug. 31, 2010

(54) ONLINE ANALYSIS DEVICE

(75) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 289 days.

(21) Appl. No.: 10/592,231

(22) PCT Filed: Mar. 16, 2005

(86) PCT No.: PCT/EP2005/002785

§ 371 (c)(1),
(2), (4) Date: Jul. 12, 2007

(87) PCT Pub. No.: WO2005/090952

PCT Pub. Date: Sep. 29, 2005

(65) Prior Publication Data

US 2007/0280413 A1  Dec. 6, 2007

(30) Foreign Application Priority Data

Mar. 16, 2004  (DE) ........................ 10 2004 012 704

(51) Int. Cl.
  *H05G 1/30* (2006.01)
  *H05G 1/56* (2006.01)
  *H05G 1/58* (2006.01)

(52) U.S. Cl. .................... 378/114; 378/115; 378/116; 378/117

(58) Field of Classification Search .............. 378/44, 378/45, 51, 53, 70, 86, 88, 91, 95, 101, 106, 378/109–112, 114–117; 73/1.79; 209/520, 209/549, 589; 250/211, 222.1, 222.2, 223 R, 250/559.4, 206, 358.1, 359

See application file for complete search history.

(56) References Cited

U.S. PATENT DOCUMENTS 2,129,383 A * 9/1938 Ulrey .......................... 378/103
2,240,037 A * 4/1941 Eaton .......................... 378/106
3,655,964 A * 4/1972 Slight .......................... 378/53
3,783,287 A * 1/1974 Fulton et al. ................. 378/112
4,386,320 A * 5/1983 Lafrance ...................... 324/410

(Continued)

FOREIGN PATENT DOCUMENTS

| EP | 0 985 926 | 3/2000 |
|---|---|---|
| EP | 1 202 045 | 5/2002 |
| JP | 11132970 | 5/1999 |
| WO | WO 95/24638 | 9/1995 |
| WO | WO 00/16078 | 3/2000 |

OTHER PUBLICATIONS

Nikitina S V et al. : "X-Ray Fluorescence analysis on the Base of Polycapillary Kumakhov Optics" Review of scientific Instruments, American Institute of Physics. New York, US, vol. 70, No. 7, Jul. 1999, pp. 2950-2956, XP000875412. ISSN: 0034-6748.

(Continued)

*Primary Examiner*—Edward J Glick
*Assistant Examiner*—Anastasia Midkiff
(74) *Attorney, Agent, or Firm*—Rabin & Berdo, PC

(57) ABSTRACT

An online analysis device, including a feed conveyor for supplying material, an X-ray tube, having an X-ray beam directed toward a measuring range on a feed conveyor, a control unit for actuating the X-ray tube, an X-ray detector that measures the radiation that interacts with, or is emitted by, the material, and a material detector for detecting material in the measuring range and generating a signal dependent thereon. To omit a mechanical shutter without reducing the service life of the tube, the material detector is connected to the control device, which controls the X-ray tube in dependence on the signal from the material detector in one of two states, where the heating current for the X-ray tube has the same order of magnitude in both states and the acceleration voltage in the first state is 5 kV to 100 kV and in the second state is less than 10 kV.

15 Claims, 2 Drawing Sheets

U.S. PATENT DOCUMENTS

Figure 1:
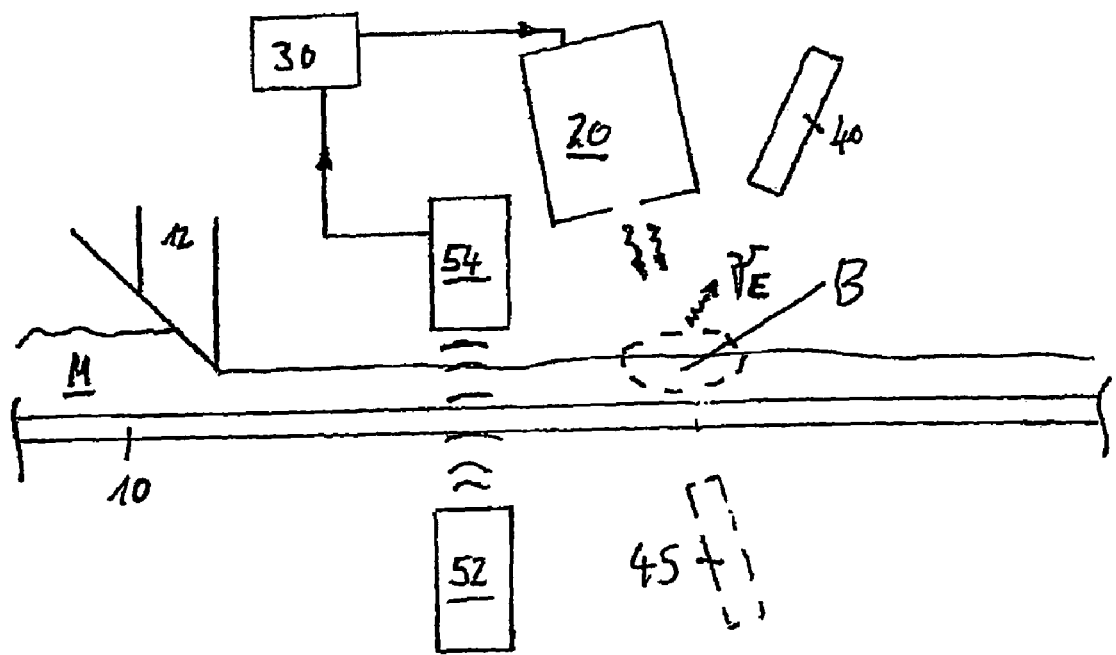

| | | | | |
|---|---|---|---|---|
| 4,593,371 | A * | 6/1986 | Grajewski | 378/207 |
| 4,827,371 | A * | 5/1989 | Yost | 361/213 |
| 4,848,590 | A * | 7/1989 | Kelly | 209/564 |
| 5,339,349 | A * | 8/1994 | Xeno | 378/101 |
| 5,398,274 | A * | 3/1995 | Komatani et al. | 378/98 |
| 5,497,008 | A | 3/1996 | Kumakhov et al. | |
| 5,721,759 | A * | 2/1998 | Raatikainen | 378/47 |
| 5,778,039 | A | 7/1998 | Hossain et al. | |
| 5,808,425 | A * | 9/1998 | Harle | 315/381 |
| 5,867,561 | A * | 2/1999 | Strasser et al. | 378/98.2 |
| 5,974,111 | A | 10/1999 | Krug et al. | |
| 6,130,931 | A * | 10/2000 | Laurila et al. | 378/45 |
| 6,233,306 | B1 | 5/2001 | Van Sprang et al. | |
| 7,099,433 | B2 * | 8/2006 | Sommer et al. | 378/53 |
| 2002/0034279 | A1 * | 3/2002 | Hirano et al. | 378/114 |
| 2004/0240606 | A1 * | 12/2004 | Laurila et al. | 378/45 |

OTHER PUBLICATIONS

Fiorini C et al.: "A new detection system with polycapillary conic collimator for high-localized analysis of X-ray fluorescence emission". Nuclear Science Symposium Conference Record, 2000 IEEE Lyon, France Oct. 15-20, 2000, piscataway, NJ, USA, IEEE, US, Oct. 15, 2000, pp. 8-28-8-31, XP010556610, ISBN: 0-7803-6503-8.

Petukhov V P et al.: "X-Ray Polarizer on the Base of Kumakhov Optics". Proceedings of the Spie, Spie, Bellingham. VA, US, vol. 3115, Jul. 31, 1997, pp. 147-152, XP009017366, ISSN: 0277-786X.

* cited by examiner

ONLINE ANALYSIS DEVICE

TECHNICAL FIELD OF INVENTION

The invention relates to an online analysis device including a feed conveyor for supplying material to be analyzed, an X-ray tube with an X-ray beam directed toward a measuring region on the feed conveyor, a control unit for actuating the X-ray tube, an X-ray detector for measuring either the X-ray radiation that interacts with the material, or the radiation emitted by the material and a material detector, which detects whether material is present in the measuring region or is supplied thereto and which then generates a signal dependent thereon.

PRIOR ART

The use of ionizing radiation for online analysis procedures is known. Such a procedure involves for the most part the irradiation of a spatially delimited measuring region of the conveyed material, so as to determine the interaction with this material. In the process, the transmitted as well as the back-scattered signal can be used, or the signal emitted as a result of excitation. In the case of X-ray fluorescence, for example, the generated characteristic X-ray luminescence radiation is measured with the aid of one or several detectors, and a conclusion concerning the material composition is reached on the basis of the measured spectrum.

As a rule, either a radioactive emitter or an X-ray tube can be used for irradiating the material. To protect against radiation, it is generally necessary to prevent rays emitted by an X-ray or gamma-ray source from escaping if no material to be measured is located in the measuring region. A movable cover is used for this, a so-called shutter, which is actuated by a material detector that detects the presence of material to be measured in the measuring region. When using a radioactive gamma source, it is absolutely necessary to provide such a mechanical shutter since a radioactive isotope naturally cannot be turned off. However, shutters are also used if an X-ray tube is used as radiation source because a frequent, complete shutdown of the X-ray tube would severely restrict its service life.

In particular when used for industrial purposes, meaning under rough and dirty environmental conditions, using a mechanical shutter can often cause problems because this shutter can jam easily, which results in a malfunction of the measuring device.

SUBJECT MATTER OF THE INVENTION

Starting with this premise, it is the object of the present invention to further modify and improve a generic device of this type, which utilizes an X-ray tube as radiation source, such that a mechanical shutter can be omitted without reducing the service life of the X-ray tube.

This object is solved with an online analysis device including a feed conveyor for supplying material to be analyzed, an X-ray tube with an X-ray beam directed toward a measuring region on a feed conveyor, a control unit for actuating the X-ray tube, an X-ray detector for measuring the X-ray radiation that interacts with the material, or the radiation emitted by this material and a material detector, which detects whether material is present in the measuring region or is supplied thereto and which then generates a signal dependent thereon, where the material detector is connected to the control unit and the control unit actuates the X-ray tube in one of two operating states, in dependence on the signal from the material detector, where the heating current of the X-ray tube has the same order of magnitude for both operating states and the acceleration voltage in the first operating state ranges from 5 kV to 100 kV and in the second operating state is less than 10 kV.

The improvement according to the invention is achieved as follows. The material detector, which detects the presence or absence of material to be measured, does not actuate a mechanical shutter, as is presently the case, but transmits a respective signal to the control unit for the X-ray tube. The control unit can generate two different operating states of the X-ray tube, namely an active state where the X-ray tube generates X-rays with the desired energy and intensity, as well as an idle state where the X-ray tube does not emit any energy quanta above a specific energy. To prevent a considerable reduction in the service life of the X-ray tube as a result of a frequent change between the two operating states, the X-ray tube is not completely shut down during the idle state. Instead, only its acceleration voltage is reduced considerably while the heating current of the hot cathode is kept as constant as possible. Some fluctuations can be tolerated in this case. Changes in the heating-current intensity of up to 50%, depending on the respectively used X-ray tube, can still be acceptable. For the most part, however, the goal should be to achieve a constancy of ±10%. To prevent space-charge effects, or at least keep these low, the acceleration voltage is not lowered to zero, but only to a value that is harmless in view of the generated radiation, for example below 5 kV.

With stabilized acceleration voltage power supply units, such as the ones used in the field of measuring technology, it is not possible in that case to keep the heating current constant by using a separate circuit because a constant anode current is generated by controlling the heating current. These supply units are therefore provided with signal-voltage inputs, designed to preset the desired values for the acceleration voltage and the anode current.

According to the invention, the X-ray tube is therefore connected such that the acceleration voltage and the anode current are simultaneously reduced in such a way that the heating current essentially remains constant. As a result, it is possible to place the tube into a non-dangerous idle state without reducing its service life, as compared to the constant operation.

According to one preferred embodiment, the control unit is provided with respectively two circuits for realizing the two operating states, wherein these circuits generate the signal voltages for the acceleration voltage and the anode current. A relay that is actuated by the material detector functions to switch between these two states.

Additional and preferred embodiments will become clear from the detailed description that follows, with reference to the drawings.

SHORT DESCRIPTION OF THE DRAWINGS

Figure 2:
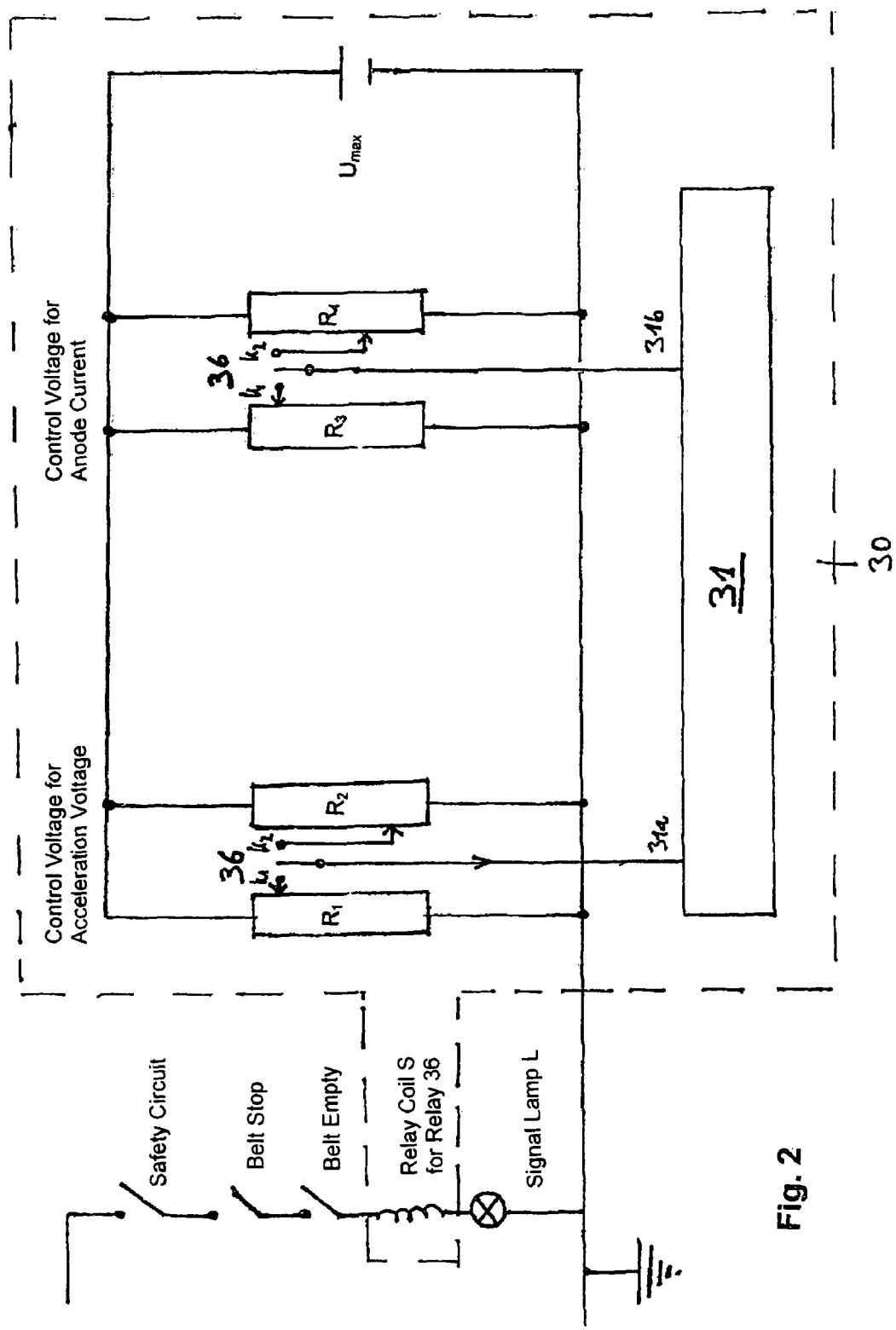

FIG. 1 Shows a schematic representation of an online analysis device for the element analysis; and FIG. 2 Shows a schematic representation of a control unit and the X-ray tube actuated by means of this control unit.

DESCRIPTION OF PREFERRED EMBODIMENTS

FIG. 1 shows a device for realizing an element analysis as example for an online analysis. A material M is conveyed on the conveyor belt 10, which in this case functions as feed conveyor, wherein the material M is initially flattened by means of the plow 12.

The X-ray tube 20 irradiates the measuring range B on the material M. An X-ray detector 40 is also directed toward the measuring range B for measuring the X-ray fluorescence radiation or the radiation scattered back from the material M. Alternatively, an X-ray detector 45 is positioned to detect the radiation transmitted through the material M. The spectra obtained in the process are used for determining the composition of the material M. Analysis may also be made by a transmission measurement or a backscattering measurement.

Upstream of the measuring region B, as seen in conveying direction, a microwave measuring section is arranged, which comprises a microwave transmitter 52 as well as a microwave receiver 54. This measuring section is designed for determining whether or not the material M is located on the conveyor belt 10. Of course, other types of detectors can also be used to meet this requirement, for example capacitive sensors. If the voltage in the idle state is only reduced enough so that the detector still receives a signal, then the signal generated by the X-ray detector 40 can be used for determining the presence or absence of material. The X-ray detector 40 would then simultaneously function as material detector within the meaning of this application.

The microwave receiver 54, which in this case functions as material detector, determines whether or not material M is located on the conveyor belt 10, based on the attenuation and/or phase displacement of the microwave signal. A signal, dependent thereon and delayed so as to correspond to the transporting speed of the belt, is subsequently transmitted by the microwave receiver 54 to the control unit 30 of the X-ray tube 20.

The control unit 30 generates the heating current and the acceleration voltage for the X-ray tube 20, and is provided with a digital interface for controlling the heating current and the acceleration voltage. Depending on the signal of the microwave receiver 54, the control unit 30 produces two different operating states for the X-ray tube 20. Firstly, there is the active state where the acceleration voltage has a value between 5 kV and 100 kV, preferably between 10 kV and 30 kV, and more preferably between 15 and 25 kV, for example, wherein 2A is a typical value for the heating current of the hot cathode. This operating state is triggered if material is detected on the conveyor belt by the microwave measuring section. If no material is detected on the conveyor belt 10, then the control unit switches to the second operating state, the idle state. Upon switching to the second operating state, the heating current is kept as constant as possible while the acceleration voltage is reduced considerably to a predetermined value below 10 kV, preferably between 500 V and 5 kV, for example 3000 volts.

FIG. 2 schematically shows an exemplary embodiment of a control unit 30, wherein the two operating states are realized by generating fixed acceleration voltages for each state, the operating state and the idle state with corresponding anode currents.

The X-ray tube must be switched to the idle state when the belt is empty or is stopped, wherein this information is provided by potential-free contacts. In a circuit, these contacts are arranged in line with the relay coil S of a double relay with two switching states and provided with contacts $K_1$, $K_1'$, and $K_2$, $K_2'$.

An indicator light L can furthermore be installed in this circuit for signaling. An additional potential-free contact should be installed in series to signal the state of safety circuit as shown in FIG. 2 and to ensure that the indicator light is turned off when the safety circuit is open and the X-ray tube 20 is in an idle state.

The control voltages for acceleration voltage and anode current are derived with the aid of 4 potentiometers from a reference voltage, which should equal the maximum control voltage Umax. R1 and R2 are used to obtain the control voltages for the active and idle states of the acceleration voltage while R3 and R4 are used to obtain the control voltages for the active and idle states of the anode current. These are fed via the relay contacts $K_1$, $K_1'$, and $K_2$, $K_2'$ to the control inputs 31a, 31b for the acceleration voltage and the anode current of the acceleration voltage generator 31. Following the adjustment of the control voltages for the desired acceleration voltage and the desired anode current in the active state, as well as for the desired acceleration voltage in the idle state, the heating current or voltage drop in the active state is measured at the tube heater and the anode current is adjusted in the idle state, such that the heating current and/or the voltage drop at the heater has the same value as for the active state. The acceleration voltage in this case cannot be adjusted to an arbitrary low level since the control for the anode current must be operated in the control range. A voltage of less than 5 kV, however, is generally easy to reach.

Of course, the required voltages can also be generated in different ways, for example from the analog outputs of a microprocessor-controlled DA converter or other microprocessor-controlled system.

The safety circuit for the control unit 30 shuts down the current to the X-ray tube completely in case of an interruption.

The invention claimed is:

1. An online analysis device, said device comprising:
    a feed conveyor for supplying material to be analyzed;
    an X-ray tube configured to generate an X-ray beam directed toward a measuring region on the feed conveyor;
    a control unit for actuating the X-ray tube;
    an X-ray detector for measuring X-ray radiation that either interacts with the material, or is emitted by the material;
    a material detector, which is configured to detect whether material is present in the measuring region or is supplied thereto and to generate a signal dependent thereon,
    wherein the material detector is connected to the control unit and the control unit actuates the X-ray tube in one of a first and a second operating state, in dependence on the signal from the material detector,
    wherein an anode current of the X-ray tube in each of the first and second operating states is respectively adjusted such that a heating current of the X-ray tube has a same order of magnitude for both the first and the second operating states,
    wherein both the acceleration voltage and the anode current are reduced in the second operating state with respect to the first operating state, and
    wherein an acceleration voltage in the first operating state ranges from 5 kV to 100 kV and in the second operating state is less than 10 kV.

2. The device according to claim 1, wherein the first and second operating states in the control unit are generated with the aid of two circuits, wherein a relay switches each of the two circuits between the first and second operating states.

3. The device according to claim 1, wherein the first and second operating states are adjusted via analog outputs of a microprocessor-controlled system.

4. The device according to claim 1, wherein the control unit comprises an acceleration voltage generator provided with a digital interface for controlling the acceleration voltage and the anode current, and wherein both the first and second operating states are adjusted by means of the digital interface.

5. The device according to claim 1, wherein the X-ray detector is configured to detect radiation transmitted through the material, and the online analysis is realized with the aid of a transmission measurement.

6. The device according to claim 1, wherein the X-ray detector is configured to detect radiation reflected by the material, and the online analysis is realized with the aid of a backscattering measurement.

7. The device according to claim 1, wherein the X-ray detector is configured to detect X-ray fluorescence.

8. The device according to claim 1, wherein a signal light indicates the operating state of the tube.

9. The device according to claim 8, wherein the signal light goes out when the tube is in the idle state and a circuit is open.

10. The device according to claim 1, wherein a fluctuation in the heating-current in the second operating state, as compared to the heating-current in the first operating state, is less than 50%.

11. The device according to claim 10, wherein the fluctuation in the heating-current in the second operating state, as compared to the heating-current in the first operating state, is less than 10%.

12. The device according to claim 11, wherein the first and second operating states in the control unit are generated with the aid of two circuits, wherein a relay switches each of the two circuits between the first and second operating states.

13. The device according to claim 11, wherein the first and second operating states are adjusted via analog outputs of a microprocessor-controlled system.

14. The device according to claim 10, wherein the first and second operating states in the control unit are generated with the aid of two circuits, wherein a relay switches each of the two circuits between the first and second operating states.

15. The device according to claim 10, wherein the first and second operating states are adjusted via analog outputs of a microprocessor-controlled system.

* * * * *